United States Patent [19]

Wegman

[11] Patent Number: 4,563,309

[45] Date of Patent: Jan. 7, 1986

[54] PRODUCTION OF CARBOXYLIC ANHYDRIDES FROM METHYL CARBOXLYATES USING RHODIUM COMPLEX CATALYSTS

[75] Inventor: Richard W. Wegman, South Charleston, W. Va.

[73] Assignee: Union Carbide Corporation, Danbury, Conn.

[21] Appl. No.: 641,219

[22] Filed: Aug. 16, 1984

[51] Int. Cl.$^4$ .............................................. C07C 51/56
[52] U.S. Cl. ..................................... 260/549; 502/166
[58] Field of Search .................. 260/546, 549; 502/166

[56] References Cited

U.S. PATENT DOCUMENTS 4,046,807 9/1977 Kuckertz ............................. 260/549
4,251,458 2/1981 Pugach ................................ 260/546

FOREIGN PATENT DOCUMENTS 055192  6/1982  European Pat. Off. .
055970  6/1982  European Pat. Off. .
055622  7/1982  European Pat. Off. .
067777 12/1982  European Pat. Off. .
0070788 1/1983  European Pat. Off. .
070787  1/1983  European Pat. Off. .
070180  1/1983  European Pat. Off. .
57-176921 of 1982 Japan .
1326014 7/1970  United Kingdom ................ 562/519
1468940 3/1977  United Kingdom .
2067556 7/1981  United Kingdom .
2067557 7/1981  United Kingdom .

OTHER PUBLICATIONS

Lomakina, L. N. et al., Chemical Abstracts, vol. 92 (1980), #208,352y.

Primary Examiner—Natalie Trousof
Assistant Examiner—L. Hendriksen
Attorney, Agent, or Firm—Bernard Francis Crown

[57] ABSTRACT

A process for the production of organic carboxylic anhydrides by the catalytic reaction of a methyl carboxylate and carbon monoxide in contact with a homogeneous catalyst system of rhodium metal atom, a phosphorus-containing ligand in which there is present at least one oxo (=O) oxygen atom attached to a phosphorus atom or a carbon atom to form a Z group and the

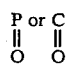

group in said Z group is located at least one carbon atom removed and preferably from 2-4 carbon atoms removed from the phosphorus atom of the molecules represented by the formulas

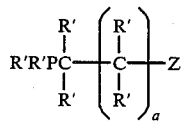

or

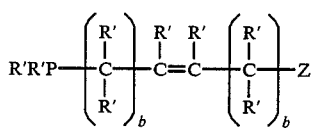

and a halogen source, under mild reaction conditions, wherein R' is aryl, alkaryl, aralkyl or alkyl, and wherein 1 or more of said R' groups can be substituted with a Z group but not more than 3 of said R' groups in the molecule are so substituted; a is an integer from 0–4; b is an integer from 0–3; and Z is P(O)R'R'; —C(O)OR" or C(O)R", wherein R" is R' or —H.

18 Claims, No Drawings

PRODUCTION OF CARBOXYLIC ANHYDRIDES FROM METHYL CARBOXLYATES USING RHODIUM COMPLEX CATALYSTS

BACKGROUND OF THE INVENTION

The production of organic compounds using synthesis gas, which is a mixture of carbon monoxide and hydrogen, or from carbon monoxide as one of the reactants has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also known that alcohols, esters, ethers, and other organic compounds can be reacted with synthesis gas or carbon monoxide to produce oxygenated organic compounds. The difficulties, however, have resided in the ability to carry out any one of these chosen reactions to produce the desired compound at acceptable efficiency, conversion rate and selectivity.

In almost all instances the reaction is generally catalyzed using a Group VIII transition metal compound as the catalyst and a halogen as the promoter. It is known that many other metal compounds and promoters can be used. In addition, the prior art has disclosed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators. Though a significant amount of literature does exist describing the production of acetic anhydride, to our knowledge it does not disclose or suggest our invention. Several of the pertinent patents in this area are discussed below.

Typical prior art processes employing rhodium catalyst to carbonylate methyl acetate, require rather harsh reaction conditions of temperature and pressure to obtain satisfactory yields of products. Such reaction conditions require use of expensive reactors, engender excessive energy cost, often lead to undesired by-products and cause excessive corrosion problems.

Various patents have issued dealing with carbonylation of methyl acetate. In U.S. Pat. No. 4,251,458, issued Feb. 17, 1981, a carboxylic acid anhydride is prepared by carbonylating a carboxylate ester employing a catalyst consisting of Rh—Cr—$CH_3I$—$ER_3$, wherein E is As and R is an organic moiety. Typical operating conditions for vapor-phase operation included employing reaction temperatures from 100° to 350° C., most preferably from 175° C. to 225° C., and reaction pressures from 1 to 5000 psia, most preferably from 150 to 500 psia. In the actual test runs reported in the examples the reaction temperature was 160° C. and the reaction pressure was 750 psia. Accordingly, this process employs a different catalyst at different operating conditions then the present invention.

British Patent Specification No. 1,468,940 issued Mar. 30, 1977, to Halcon Research and Development Corporation discloses a catalyst for carbonylating methyl acetate to form acetic anhydride wherein the catalyst consists of Rh-Cr-$CH_3I$. The process is carried out at reaction temperatures of 175° C. and reaction pressures on the order of 350 psia. The patent neither discloses nor suggests employing phosphine ligands as a key ingredient in the catalyst. In general, acetic anhydride was formed at the rate of less than about 1.25 moles per liter per hour. This process does not utilize the mild reaction conditions of the instant process.

British Patent Specification Nos. 2,067,556 ('556) and 2,067,557 ('557), both issued July 30, 1981 to Halcon Research and Development Corporation disclose preparation of acetic anhydride from methyl acetate in a carbonylation process employing a catalyst system different from that of the present invention. In the '556 Patent the catalyst was Rh—Hf—$CH_3I$—$ER_3$, while in the '557 Patent the catalyst was Rh—Zr—$CH_3I$—$ER_3$, wherein E is N, As, P and Sb. In the experiments reported in the Examples the reaction temperatures were on the order of 160° C. and the reaction pressures were on the order of 700 psig. Although reaction temperatures as low as 100° C. and reaction pressure as low as 15 psig were recited in the specification, no examples having such low temperatures or low pressures were provided.

In European Patent Application No. 055,622 published July 7, 1982, a catalyst system for the carbonylation of methyl acetate to acetic anhydride is disclosed. The catalyst includes nickel; a halide; the ligand $ER_3$, wherein E is N, P, As, Sb and R is an organic moiety and a co-catalyst (N) which is a Group IA, IIA, IIIB or IVB metal. Operating temperatures can vary from 100° to 250° C., while operating pressures were from 40 to 2200 psig. The experiments reported in the examples were generally carried out at reaction temperatures from 180° C. to 200° C. and reaction pressures from 1000 to 1500 psig with acetic acid as a solvent. The ligand employed in most runs was 2, 4-lutidine. This process employs higher operating temperatures and pressures and a different catalyst than the present process.

European Patent Application No. 055,192, published June 30, 1982 teaches preparation of acetic anhydride by carbonylation of methyl acetate employing, as the catalyst system, nickel, methyl iodide; an ionic iodide; a carboxylate co-catalyst—LiOAc and a carboxylic acid solvent, such as acetic acid. The reactions were generally carried out at a reaction temperature of about 180° C. and a reaction pressure on the order of 1000 psig. Accordingly, the catalyst and reaction conditions were different from those of the present invention.

In European Patent Application No. 055,970 published July 14, 1982 a process similar to that disclosed in European Patent Application No. 055,192 is disclosed, with the exception that the ionic halide component of the catalyst is $R_4EI$ wherein E is N or P. The reaction is typically carried out at operating temperatures on the order of 180° C. and operating pressures on the order of 1300 psig.

European Patent Application No. 067,777 published Dec. 22, 1982 is directed to the carbonylation of methyl acetate with a Co-Ru-MI-MOAc catalyst to obtain acetic anhydride. The halogen is specifically an ionic iodide. MI, as opposed to a covalent iodide, such as $CH_3I$. MI is typically a phosphonium salt, $[R_4P]I$, such as $[CH_3(Ph)_3P]I$. A fourth component of the catalyst is a metal acetate, where the metal can be an alkali metal.

The reaction is typically carried out at reaction temperatures from 180° to 210° C. and at reaction pressures on the order of 3700 psig. There is no disclosure or suggestion of the instant novel rhodium complex catalyst. In addition, the actual operating parameters of temperature and pressure for that process are not the mild operating parameters of the present process.

European Patent Application No. 070,788 published Jan. 26, 1983 relates to the formation of acetic anhydride by the carbonylation of methyl acetate with a Co—Cr, Mo, or W—MI catalyst. MI represents an ionic iodide such as [CH$_3$(Ph)$_3$P]I or an alkali, alkaline, lanthanide or actinide metal halide. The process described is similar to that illustrated in European Patent Application Nos. 067,777 and 070,787. The reaction is normally carried out at temperatures on the order of 210° C. and at operating pressures on the order of 3700 psig. There is no disclosure or suggestion of the novel rhodium complex catalyst of the instant invention or of the ability to employ such catalyst at mild operating conditions.

In European Patent Application No. 070,180 published Jan. 19, 1983 there is disclosed a process for carbonylation of methyl acetate to acetic anhydride. The catalyst employed is Ni—I—Gp—IV/Gp I/Gp II catalyst, and a typical catalyst is Ni—CH$_3$I—Sn (OAc)$_2$—LiOAc. While the application theoretically discloses that broad ranges of temperatures and pressures are possible, nonetheless all the actual runs reported are carried out at temperatures on the order from 175° to 200° C. and at operating pressures from 980 to 1400 psig. Accordingly, it is clear that both the catalyst and actual operating parameters are different from the far milder operating conditions and the unique rhodium complex catalyst of the present invention.

Japanese Patent Publication No. 57-176921, filed by Showa Denko is directed to a vapor phase process for the carbonylation of methyl acetate to acetic anhydride. The catalyst employed is rhodium supported on a porous carrier, such as activated carbon. The present catalyst is a different rhodium complex. Methyl iodide is co-fed with CO and methyl acetate. The range of theoretical operating temperature is generally said to be from about 200° to 500° C. and the preferred operating pressures are said to be from 14 to 450 psig. In the reported test runs, however, the operating temperatures of the relevant Examples ranged from 200° to 230° C. and the operating pressures were in the range from 150 to 220 psig. Such conditions are not the mild conditions of the instant process.

As shown above, numerous Group VIII metals and a halide promoter are known to catalyze the carbonylation of methyl acetate to acetic anhydride. For the most part such catalysts operate at relatively harsh reaction conditions of temperature and pressure. Rhodium is known to act at less harsh pressure conditions. To obtain reasonable reaction rates, however, higher operating temperatures of greater than 160° C. and usually more than 180° C., are required.

SUMMARY OF THE INVENTION

A process for the production of organic carboxylic anhydrides has been discovered. The process can produce organic anhydrides of the formula

[RC(O)O(O)CCH$_3$], wherein R is a monovalent hydrocarbyl group, including an alkyl group having from 1 to 30 carbon atoms or aryl, aralkyl or alkaryl groups having from 6 to 10 ring carbon atoms with from 1 to 10 carbon atoms in the alk-moiety thereof or alkenyl having from 2 to 30 carbon atoms; and preferably an alkyl group having 1 to 10 carbon atoms. The process includes the catalytic reaction of a methyl carboxylate of the formula RC(O)OCH$_3$ and carbon monoxide in contact with a homogeneous catalyst system at mild reaction conditions.

The catalyst system consists essentially of rhodium metal atom, a halogen source and a phosphorus containing ligand in which there is present at least one oxo (=O) oxygen atom attached to a phosphorus atom or a carbon atom to form a Z group and the

group in said Z group is located at least one carbon atom removed and preferably from 2-4 carbon atoms removed from the phosphorus atom of the molecules represented by the formulas

or

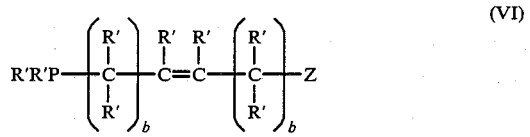

wherein R' is hydrogen unsubstituted or substituted (e.g. halogen, nitro, amino, etc.) aryl, aralkyl or alkaryl having from 6 to 10 ring carbon atoms and the alkyl moiety of the aralkyl or alkaryl group has from 1 to 10 carbon atoms and preferably 1 to 4 carbon atoms; or alkyl having from 1 to 10 carbon atoms and preferably 1 to 4 carbon atoms; and wherein 1 or more of said R' groups can be substituted with a Z group but not more than 3 of said R' groups in the molecule are so substituted; a is an integer from 0–4; b is an integer from 0–3; and Z is a member selected from the group consisting of

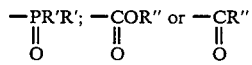

wherein R" is R' or —H. R' can be the same or different. The reaction conditions are mild, usually at reaction temperatures less than about 150° C. and at reaction pressures less than about 250 psig.

The halogen source can be a single compound, such as lithium iodide, or a mixture of compounds as lithium iodide and methyl iodide.

Under catalytic conditions it is understood that a novel monocarbonyl rhodium complex of the formula A:

Rh(CO)X(R'R'PGZ)    [A]

wherein X is halogen and R' and Z are as before, and wherein G represents the two

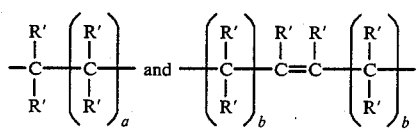

groups of formulas (V) and (VI), is formed in-situ.

The novel rhodium complex of the invention has been synthesized, isolated and characterized. The synthesized rhodium complex may be prepared in advance and used in place of the in-situ formed catalyst.

The Formula A rhodium complex is understood to be subject to the addition of a second mole of carbon monoxide to form a second catalytic dicarbonyl rhodium complex of Formula B and having the general formula:

$$Rh(CO)_2X(R'R'PGZ) \qquad [B]$$

The Formula B rhodium complex can be prepared in advance of the process rather than being formed in-situ from Formula [A].

It has been found that the combination of the rhodium complex catalyst and halogen source provides high efficiency, high conversion or rate and high selectivity never before achieved at such mild conditions.

DESCRIPTION OF THE INVENTION

In the catalytic reactions of synthesis gas or carbon monoxide in processes to produce oxygenated organic compounds there are several criteria required of the catalyst. The catalyst must be as stable as possible, it should have a high activity or conversion rate, and it should have as high a selectivity for the desired product as possible.

Stability of the catalyst relates to how long the catalyst remains functional before either breaking down or losing its catalytic effect.

Activity or conversion rate relates to the amount of reactants the catalyst converts to product per unit of time, generally expressed in g. mole per liter per hour (g mole/1/hr) or mole per hour (Mhr$^{-1}$).

Selectivity relates to the quantity of desired product produced, generally expressed in mole percent, based on the total amount of both desired products and undesired products produced.

The goal to be achieved is high values for all three criteria and continued efforts are being made to find new catalyst compositions to reach this goal without having a significant detrimental effect on the overall process. Toward this goal the prior art has developed catalyst systems containing a wide variety of metal atoms, promoters and activators, in many cases with diverse other components added. Though these catalyst systems are effective they usually require rather harsh reaction conditions and, accordingly, improvements is always desirable. Other factors having an impact on the process are the reaction temperature and reaction pressure. In the past it was generally thought necessary to increase these variables to improve overall selectivity and conversion.

The present invention is based on the unexpected and unpredictable discovery that the herein defined rhodium-catalyst systems which contain the specifically defined ligands produce carboxylic anhydrides from methyl carboxylates and carbon monoxide at unexpectedly high efficiency, selectivity and conversion rates at mild reaction conditions. Optionally, a solvent and/or diluent as acetic acid can also be present.

In the process of our invention a methyl carboxylate is reacted with carbon monoxide in the presence of the inventive catalyst system. This system produces commercially desirable anhydrides at unexpectedly high efficiency, conversion rate and selectivity, with a minimum of by-products and under mild reaction conditions. The overall reaction that occurs in the production of anhydrides is theoretically:

$$RC(O)OCH_3 + CO \rightarrow RC(O)O(O)CCH_3$$

In the above formula R is a monovalent hydrocarbyl group. It can be an alkyl group having from 1 to 30 carbon atoms, preferably from 1 to 15 carbon atoms, and most preferably from 1 to 3 carbon atoms; an alkenyl group having from 2 to 30 carbon atoms, preferably from 2 to 15 carbon atoms and most preferably from 2 to 5 carbon atoms; or an aryl, aralkyl or alkaryl group having 6 or 10 ring carbon atoms, as phenyl and naphthyl, with from 1 to 10 carbon atoms, preferably 1 to 4 carbon atoms, in the alk-moiety thereof. The especially preferred R group is alkyl.

Examples of typical methyl carboxylic acid esters of the invention are methyl butyrate, methyl decanoate, methyl 2-ethylhexanoate, methyl stearate, methyl benzoate, methyl 2-phenylacetate, methyl acrylate, methyl napthoate and the like.

The R group can be linear or branched and it can be unsubstituted or substituted with groups which will not have an adverse effect on the reaction. The most preferred methyl carboxylates are methyl acetate, ethyl acetate and propyl acetates with the especially preferred one being methyl acetate.

The rhodium component of the catalyst system can be supplied from any number of sources, many of them are known to those of ordinary skill in the art. Thus, it is not necessary for an understanding thereof to specifically enumerate every suitable type and every specific compound since any of the known rhodium compounds can be used.

The essential rhodium component of the catalyst system of the present invention may be provided by introducing into the reaction zone a compound of rhodium or may be provided by introducing into the reaction zone, rhodium. Among the materials which may be charged to the reaction zone to provide the rhodium component of the catalyst system of the present invention are rhodium metal, rhodium salts and oxides, organo rhodium compounds, coordination compounds of rhodium, and the like. Specific examples of materials capable of providing the rhodium constituent of the catalyst system of the present invention may be taken from the following non-limiting partial list of suitable materials.

RhCl$_2$
RhBr$_3$
RhI$_2$
RhCl$_3$·3H$_2$O
RhBr$_3$·3H$_2$O
Rh$_2$(CO)$_4$Cl$_2$
Rh$_2$(CO)$_4$Br$_2$
Rh$_2$(CO)$_4$I$_2$
Rh$_2$(CO)$_8$

Rh metal
Rh(NO$_3$)$_3$
[(n—C$_4$H$_9$)$_4$N][Rh(CO)$_2$X$_2$] where X=Cl—, Br—, I—
[(N—C$_4$H$_9$)$_4$As]$_2$[Rh(CO)$_2$Y$_4$] where X=Cl—, Br—, I—
[(n—C$_4$H$_9$)$_4$P][Rh(CO)I$_4$]
Rh$_2$O$_3$
[Rh(C$_3$H$_4$)$_2$Cl]$_2$
K$_4$Rh$_2$Cl$_2$(SnCl$_2$)$_4$
K$_4$Rh$_2$Br$_2$(SnBr$_3$)$_4$
K$_4$Rh$_2$I$_2$(SnI$_2$)$_4$ The rhodium metal atom concentration can vary over a wide range. Enough metal atom must be present to achieve reasonable reaction rates; however, an excess may, on occasion, result in undesired by-products formation. The mole ratio of rhodium atom to methyl carboxylate can vary from 1:25 to 1:20,000, the preferred range is from about 1:40 to 1:1000, with the most preferred range being from about 1:100 to 1:500. The amount used is not a critical feature in this invention and higher rhodium concentrations are acceptable but are influenced by economic considerations.

In general the rate of reaction increases with increasing rhodium concentration. For most purposes it is sufficient to employ a rhodium concentration from about 0.0001 to 1 mole per liter, preferably from about 0.01 to 0.1 mole per liter, although higher or lower concentrations may be utilized, depending, in part, upon economic considerations.

The second component of the catalyst system is a halogen source which contains a metal halide employed alone, or, more preferably, in combination with a halide promoter. The metal halide which is a Group I, II, V, VI, or VIII metal halide must be present. The preferred metal halide is a lithium halide.

The halide promoter component of the halogen source can be a halogen compound containing iodine, bromine or chlorine or two or more of the same, or the elemental halogen per se, or any mixtures of compounds and/or elements. Their identities are well known to those of ordinary skill in this art.

The preferred halide promoters are methyl iodide and iodine. As indicated, other suitable halogen compounds are well known to those of average skill in this art; thus a complete listing is not necessary for their comprehension.

The lithium halide can be charged directly to the process or it can be formed in-situ by any combination of lithium compound and halide component that will result in the formation of lithium halide during the reaction. Lithium bromide can also be used, but lithium iodide is the preferred lithium halide.

The presence of lithium iodide in conjunction with a halide promoter, such as methyl iodide, is a preferred embodiment of this invention. Direct charge of lithium iodide is the preferred form. However, any convenient combination of compounds for in-situ formation of lithium iodide can be used. This includes the use of lithium carboxylates, carbonates and the like with a halogen compound such as iodine or an alkyl halide. A suitable combination for in-situ formation is lithium carboxylate (with the same functionality as the instant methyl carboxylate ester feed-stock) and an alkyl halide. Illustrative of suitable halogen sources there can be mentioned barium iodide, hydriodic acid, cobalt iodide, potassium iodide, lithium iodide, sodium iodide, calcium iodide, ammonium iodide, methyl iodide, ethyl iodide, propyl iodide, 2-ethylhexyl iodide, n-decyl iodide, acetyl iodide, propionyl iodide; the organic ammonium iodides of the formula R'''$_4$NI and the organic phosphonium iodides of the formula R'''$_4$PI in which R''' is alkyl, saturated or unsaturated, substituted or unsubstituted, having from 1 to about 10 carbon atoms or aryl, unsubstituted or substituted, having from 6 to 10 ring carbon atoms such as trimethyl ammonium iodide, tetraethyl ammonium iodide, tetra-2-ethylhexyl ammonium iodide, tetraphenyl ammonium iodide, tetramethyl phosphonium iodide, tetra-2-ethylhexyl phosphonium iodide, tetrapropyl phosphonium iodide, methyltriphenyl phosphonium iodide, and the like; methylammonium iodide, tri-p-tolyl-ammonium iodide, decylammonium iodide, ethylphosphonium iodide, triphenyl-phosphonium iodide, tricyclohexylphosphonium iodide, tri-p-tolyphosphonium iodide, and the like.

Also useful are bromine and its corresponding compounds and chlorine and its corresponding compounds. Any source of halogen atom can be used provided that it does not have a deleterious effect on the reaction.

The amount of halogen source charged depends, in part, on the amount of rhodium employed. Sufficient halogen source must be present to exert a promoting effect on the reaction and to result in high efficiency, conversion rate and selectivity to the desired anhydride. Where the halogen source is a lithium halide, such as lithium iodide, solely, the mole ratio of LiX:Rh may vary widely. For the preferred LiI, the mole ratio of LiI:Rh ranges from 1:200 to 200:1 and, particularly, from 1:1 to 128:1. When the halogen source is a mixture of, for example, lithium iodide and methyl iodide, then the same LiI:Rh ratio is maintained, and the CH$_3$I:LiI mole ratio ranges from 1:200 to 200:1 and more preferably, from 10:1 to 1:10.

The third component of the catalyst system is a phosphorus-containing ligand of the formula R'R'PGZ, wherein R' and G are as previously defined and Z is selected from the group:

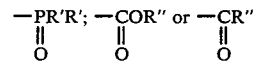

The R' aryl, aralkyl or alkaryl groups have from 6–10 ring carbon atoms; The alkyl moiety of the alkaryl or aralkyl group has from 1–10 carbon atoms, preferably 1–4 carbon atoms. The alkyl group has from 1 to 10 carbon atoms and preferably 1–4 carbon atoms.

In a first embodiment, the phosphorus-containing ligand has the general formula

wherein R' and G are as before. The R' groups can be alike, different or mixed. Typical ligands of this embodiment include:

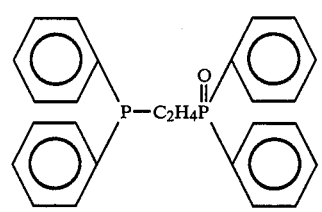

(1)

-continued

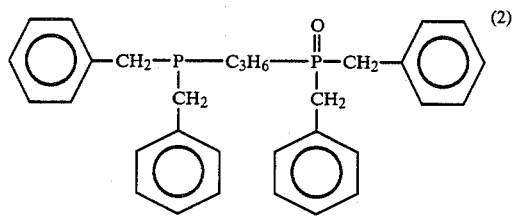 (2)

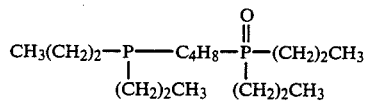 (3)

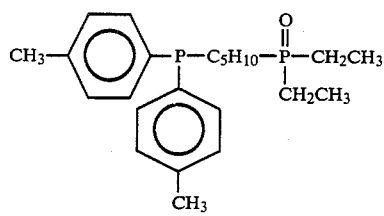 (4)

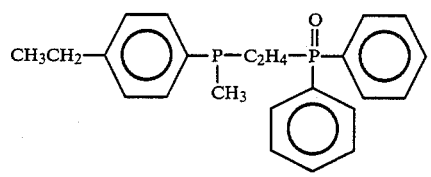 (5)

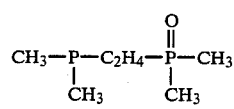 (6)

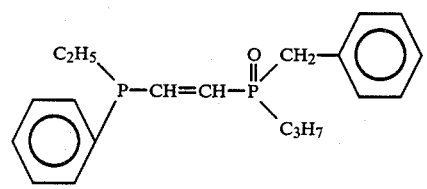 (7)

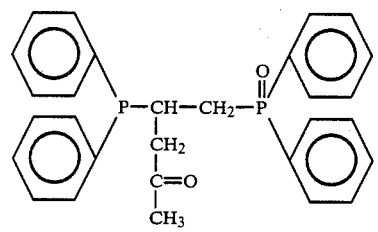 (8)

An especially preferred ligand of Formula (I) is

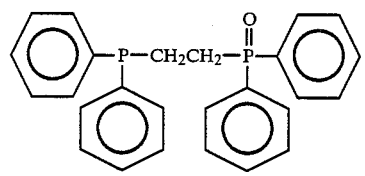

In a second embodiment the phosphorus-containing ligands have the general formula (II):

R'R'PGC(O)OR"

and in third embodiment the phosphorus-containing ligands have the general formula III:

R'R'PG CR"

wherein R' and G are as before; and R" is R' or —H.

Typical examples of formula II compounds include:

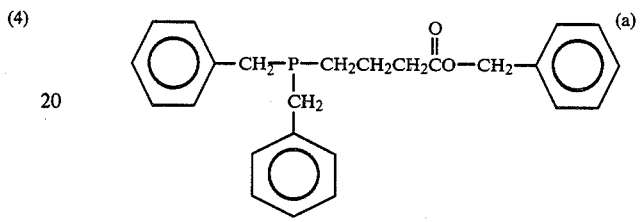 (a)

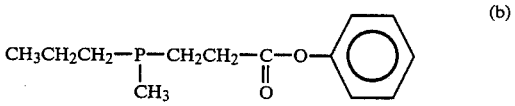 (b)

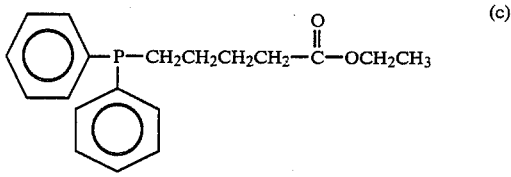 (c)

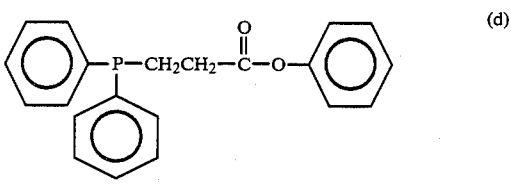 (d)

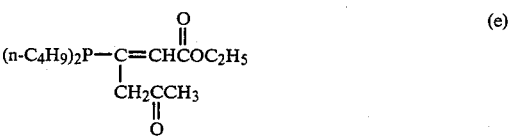 (e)

Typical examples of formula (III) compounds include:

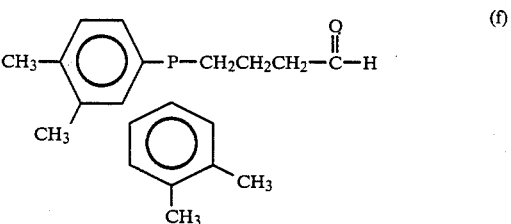 (f)

(g)

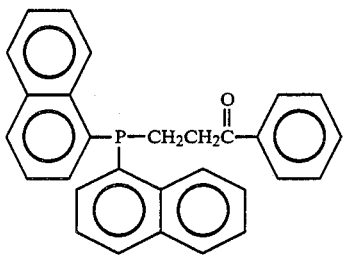

(h)

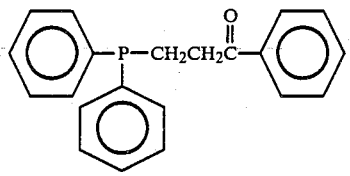

(i)

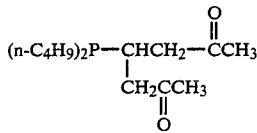

It has been found that conventional ligands such as $ER_3$ (E=P,N, As and R=organic moiety) and chelating agents, such as $R'R'P(CH_2)_nPR'R'$ tend to deactivate the catalyst system at low temperature and pressure.

The reactive rhodium complex of formula A can be generally prepared and isolated by the typical reaction involving the dissolution of $[Rh(CO)_2Cl]_2$, or any other halide compound of this formula, in an inert solvent, such as dichloromethane, benzene, toluene and like, under inert atmospheric conditions. A stoichiometric amount of phosphine, based on the rhodium content, is added, and the mixture is stirred at a temperature of from about 0° C. or less up to the boiling point of the mixture, or higher. The reaction can be carried out at subatmospheric, atmospheric or superatmospheric pressure. The temperature and pressure are not critical.

Stirring is continued until the reaction is complete and this, as is obvious, will be dependent upon the specific reactants employed, reaction conditions used and the size of the batch. At completion of the reaction, one can, if so desired, separate the complex from the diluent using conventional procedures.

The structure of the formula A complex, identified herein as [A'] is believed to be (schematically) as follows:

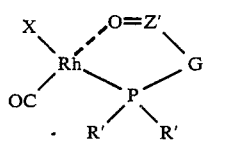

[A']

wherein R', G and X are as before and Z' is —P—R'R'; —COR" or —CR" and wherein R" is R' or —H. The formula A complex may be formed in either the cis- or trans-geometrical isomer, wherein the X— and OC— moieties in complex A' are as they appear or are reversed.

Analysis to date of complex A' by NMR and IR has demonstrated the cis-isomer as the form present at room temperatures.

In the catalytic reaction for the production of the anhydrides the catalyst complex can be prepared and then added to reactor or it can be formed in situ during the reaction.

Carbon monoxide may be combined with Formula A complexes to form Formula B complexes. That complex may be represented, schematically by Formula B' as follows:

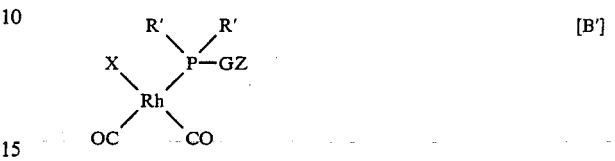

[B']

wherein X, R', G and Z are as before.

If desired, Formula B complexes may be prepared in advance of the process by the carbonylation of Formula A complexes or the like. Formula B complexes have not yet been isolated, but, from spectral analyses of the reaction mixture appear to have the indicated structure. Other procedures which will be apparent to those skilled in this art may also be utilized to make Formula B complexes.

The concentration of ligand charged to the catalytic reaction can be varied from a molar ratio of ligand to rhodium of from about 50:1 to 1:50, preferably from 10:1 to 1:10 and most preferably from about 3:1 to 1:1.

The reaction is carried out at a mild reaction temperatures, up to about 160° C. and preferably from about 50° C. to 150° C. and, most preferably, from 105° C. to 125° C.

The reaction pressure employed is much milder than those generally employed. The pressure of the reaction generally is up to about 450 psig and preferably, from 50 psig to 350 psig, most preferably from 100 psig to 250 psig.

The reaction time varies depending upon the reaction parameters, reactor size and charge, and the individual components employed at the specific process conditions. The reaction can be a batch or continuous reaction. In addition one can optionally have a solvent present. Many essentially inert solvents are known as useful, essentially inert, diluents and illustrative thereof one can mention 1,4-dioxane, the polyethylene glycols di-ethers or esters, diphenyl ether, sulfolane, toluene, carboxylic acids as well as any other diluent or solvent which does not interfere with the reaction to any significant extent. When a solvent is employed, the preferred one is acetic acid. Acetic acid is effective in preventing rate decreases and catalyst precipitation during long term operations.

PREPARATION EXAMPLE I

The reactions were carried out in any convenient equipment; for example, a glass pressure bottle (Fisher Porter ®) or in a 300 cc reaction autoclave. In the case of the glass bottle the reagents can be charged in numerous ways. For example, all the solid components (LiI, Rh, phosphine ligand) are first charged, the bottle is then purged with CO and degassed methyl acetate and $CH_3I$ are then added under a CO flow. Alternatively, a complex such as $RhCO(I)[Ph_2PCH_2CH_2P(O)Ph_2]$ dissolved in methyl acetate can be added to the bottle which contains LiI and $CH_3I$. In any event, once all the reagents are added, the bottle is pressured to 30 psi with CO, sealed by means of a valve, and heated to the desired temperature, usually between 105° C. and 125° C. At the desired temperature the pressure is adjusted to the reported value with CO. The bottle was repressurized after every 10 psi uptake. The reaction was typically carried out from 0.5 to 4.0 hours.

PREPARATION EXAMPLE II

The following procedures were used with the 300 cc autoclave. The autoclave is equipped with a magnetically driven agitator, internal cooling coil, gas sampling port and electric heater. Prior to charging the reactants, the autoclave is washed with methanol at 100° C. at 500–1,000 psig syn gas for 30 minutes. The reactor is drained, opened, rinsed with acetone, and dried with nitrogen. To the open and cleaned reactor is charged first the liquid and then the solid reactants. The reactor is closed, purged with CO and then pressurized with CO usually to 20–30 psi. With agitation (750 rpm's) the reactor contents are heated to the desired temperature, usually between 105° C. and 125° C., in about 45 minutes. Next the reactor is pressured with CO to the desired pressure, usually between 100 and 200 psi, and repressured after every 30 psi uptake. The reactor is maintained at the desired temperature for a specified time period, usually between 0.5 to 5.0 hours. At the end of the specified time period the reactor contents are normally cooled to 10° C. A vapor phase sample is taken and analyzed by gas chromatography for CO, $H_2$, $CO_2$, and $CH_4$ plus other gaseous hydrocarbons. The reactor gas phase is vented through two dry ice-acetone traps and then a 2.5 gallon saturated solution of calcium hypochlorite to remove iron and/or nickel carbonyls. The reactor is pressurized three times with 90 psig nitrogen and vented through the same trap-vent system.

The reactor contents from the glass pressure bottle or 300 cc autoclave were dumped into a chilled bottle flushed with $N_2$. The liquid proucts were analyzed via a Varian 3700 gas chromatograph equipped with a Supelco DB 1701 30M capillary column or a HP-5880 gas chromatograph equipped with a 1 percent FFAP on Tenax column.

The following examples serve to further illustrate this invention.

EXAMPLE 1

The following components were charged to a 100 cc Fisher Porter Bottle ®:
[Rh(CO)$_2$Cl]$_2$: 0.09 g (Rh=0.46 mm)[a]
Ph$_2$PCH$_2$CH$_2$P(O)Ph$_2$: 0.23 g (0.55 mm)
LiI: 2.0 g (14.9 mm)
Methyl Acetate: 6.8 g
[a]mm is millimoles In the ligand, Ph represents a phenyl group. Following the procedures described in Preparation Example I, the reactor was maintained at 118° C. and 110 psi total operating pressure for 1.0 hour. During this time period the pressure was maintained by addition of carbon monoxide, as needed. At the end of the reaction the liquid product mixture consisted of:

| Component | Wt % |
| --- | --- |
| Methyl iodide | 4.4 |
| Methyl acetate | 66 |
| Acetic acid | 3 |
| Acetic anhydride | 26 |

The calculated rate to acetic anhydride was 2.5 Mhr$^{-1}$ and the selectivity was 92%. The methyl acetate conversion was 20%.

Similar results are obtained when other rhodium sources are substituted; such as Rh$_2$(CO)$_4$Br$_2$, Rh(CO)$_2$AcAc*, K$_4$Rh$_2$I$_2$(SnI$_2$)$_4$, [(n—C$_4$H$_9$)$_4$N][Rh(CO)$_2$I$_2$]
*AcAc=acetylacetonate

EXAMPLE 2

The reaction was carried out in accordance with the procedure of Example 1, except the reaction temperature was maintained at 100° C. for 2.0 hours. Very little gas consumption occurred and only trace amounts of acetic anhydride were found in the recovered reaction mixture. Accordingly, while reaction temperatures less than 100° C. can be employed if reduced yields are acceptable, best results are at temperatures above about 105° C.

EXAMPLE 3

The reaction was carried out in accordance with the procedure of Example 1, except that no Ph$_2$PCH$_2$CH$_2$P(O)Ph$_2$ was utilized. There was no observable gas consumption. Acetic anhydride was not detected in the recovered reaction mixture. The results demonstrate the criticality of employing the ligand of the invention to obtain yields of anhydride at mild operating conditions.

EXAMPLE 4

A run was carried out employing the same amounts of reagents as in Example 1. The Example 1 procedure was followed. The reaction time was increased to 2.5 hours. Gas consumption was steady for the first 1.5 hours, then markedly slowed. The product mixture contained solids. The calculated acetic anhydride rate was 1 Mhr$^{-1}$ with a methyl acetate conversion of 28 percent. The results demonstrate that long term operation will generally result in rate decreases and, in the absence of a solvent, catalyst precipitation.

EXAMPLE 5

In order to illustrate another embodiment of the invention the following amounts of reagents were utilized in the procedure of Example 1:
[Rh(CO)$_2$Cl]$_2$: 0.09 g (Rh=0.46 mm)
Ph$_2$PCH$_2$CH$_2$P(O)Ph$_2$: 0.23 g (0.55 mm)
LiI: 3.0 g (22.3 mm)
Methyl Acetate: 10.7 g
Acetic acid: 2.0 g The reaction was carried out at 117° C. and 145 psi total operating pressure for 5.0 hours. Gas consumption was steady throughout the entire reaction. The product mixture was a homogeneous liquid and contained the following amounts:

| Component | Wt % |
| --- | --- |
| Methyl iodide | 2.3 |
| Methyl acetate | 32 |
| Acetic acid | 15 |
| Acetic anhydride | 49 |

The calculated acetic anhydride rate is 2.1 Mhr$^{-1}$ with a methyl acetate conversion of 73 percent.

This example demonstrates the enhanced results obtained when a solvent as acetic acid is employed. Its presence generally improves the rate and eliminates catalyst precipitation, especially during long term operation. In addition the run illustrates that lithium iodide can be employed as the sole halogen source.

EXAMPLE 6

A glass reactor was charged with $[Rh(CO)_2(Cl)]_2$ (0.09 gm. Rh=0.46 mm), $Ph_2PCH_2CH_2P(O)Ph_2$ (0.23 gm, 0.55 mm) and acetic acid (1.0 gm) along with various amounts of $CH_3I$ and/or LiI and methyl acetate. The reaction was carried out at 115° C. and 145 psi total operating pressure in accordance with Example 1. The results are summarized below.

| Run No. | LiI mm | $CH_3I$ mm | MeOAc gm | $^a Ac_2O$ Rate $Mhr^{-1}$ |
|---|---|---|---|---|
| 1 | 30 | — | 5.9 | 1.9 |
| 2 | 22 | — | 5.8 | 1.9 |
| 3 | 15 | — | 5.8 | 1.4 |
| 4 | 22 | 32 | 5.8 | 2.4 |
| 5 | 22 | 48 | 4.9 | 2.1 |
| 6 | 34 | 48 | 4.9 | 1.7 |
| 7 | — | 17 | 5.8 | 0.05 |

$^a Ac_2O$ is acetic anhydride.

The above data demonstrates that wide ratios of LiI and $CH_3I$ can be utilized. The best results are obtained when $CH_3I$ and LiI are used together. There is very little reaction, when only $CH_3I$ is used.

When other promoters are substituted for $CH_3I$, such as hydriodic acid, ethyl iodide, trimethyl ammonium iodide, methyl bromide, methyl triphenyl phosphonium chloride and the like, similar results are obtained.

EXAMPLE 7

A run was carried out at two different reaction temperatures. The following amounts of reagents were charged to the Fisher Porter bottle of Preparation Example I.

$[Rh(CO)_2Cl]_2$: 0.09 g (Rh=0.46 mm)
$Ph_2PCH_2CH_2P(O)Ph_2$: 0.23 g (0.55 mm)
$CH_3I$: 4.56 g (32 mm)
LiI: 3.0 g (22.3 mm)
Methyl Acetate: 5.82 gm
Acetic acid: 2.0 gm The reaction was carried out at 145 psi. At 115° C. the $Ac_2O$ rate was 2.36 $MH^{-1}$. At 135° C. the $Ac_2O$ rate was 2.2 $Mhr^{-1}$. The rates are based on gas uptake.

This run demonstrates that various temperatures within the scope of the invention can be employed.

EXAMPLE 8

A 300 cc autoclave was charged with the following components:

$Rh(CO)_2AcAc^c$: 1.8 (7.0 mm)
$Ph_2PCH_2CH_2P(O)Ph_2$: 2.89 g (7.0 mm)
$CH_3I$: 45.6 g (321 mm)
Methyl Acetate: 63 g
Acetic acid: 15 g
LiI: 20 gm (149 mm)
$^c AcAc$ is acetylacetonate The reaction was carried out at 118° C. and 150 psi total operating pressure in accordance with the Preparation Example II autoclave procedure.

In this run $Rh(CO)_2AcAc$ was utilized as the Rh source. Also, larger amounts of reagents were employed relative to the runs conducted in the glass reactor. Accordingly it is seen that the reaction was successfully scaled up. The calculated rate to acetic anhydride was 1.2 $Mhr^{-1}$. When other ligands such as $$Ph_2P(CH_2)_2\overset{\overset{O}{\|}}{C}OCH_2CH_3;$$

$(CH_3)_2P(CH_2)P(O)(CH_3)_2$:   $(Tolyl)_2P(CH_2)_2$-$C(O)OCH_2CH_3$ and $(Benzyl)_2P(CH_2)_2P(O)(Benzyl)_2$ are substituted for the ligand of Example 8, similar results are obtained.

EXAMPLE 9

The glass reactor was charged with $[Rh(CO)_2CL]_2$ (Rh=0.46 mm), $CH_3I$(32.0 mm), LiI (22.7 mm), acetic acid (1.0 g), methyl acetate (5.82 g) and various amounts of $Ph_2PCH_2CH_2P(O)Ph_2$. The reaction was carried out at 115° C. and 145 psi total operating pressure. The results are summarized below.

| Run | $Ph_2PCH_2CH_2P(O)Ph_2$ mm | Acetic Anhydride Rate $Mhr^{-1}$ |
|---|---|---|
| 1 | 1.57 | 2.3 |
| 2 | 2.4 | 2.2 |
| 3 | 4.8 | 1.9 |

The MeOAc conversion was maintained at 40 percent in each run. In each case the liquid product was a homogeneous solution. For Run 2 the composition of the liquid product is given below.

| Component | Wt % |
|---|---|
| $CH_3I$ | 24.4 |
| MeOAc | 29.7 |
| HoAc | 1.1 |
| $Ac_2O$ | 44.0 |

No other products were detected via gas chromatography analysis.

EXAMPLE 10

Preparation of Complexes

A series of runs was performed using the following general procedure to produce the complexes of formulas A' and B'. A solution of 2.5 millimoles (mm) of $C_6H_5PCH_2P(O)(C_6H_5)_2$ in 10 ml methylene chloride was added to a solution of 1.25 mm $[Rh(CO)_2Cl]_2$ in 10 ml methylene chloride. The mixture was allowed to stir for 10 minutes and the methylene chloride was removed under vacuum. The residual viscous oil was redissolved in 10 ml methylene chloride and the solvent evaporated again. This procedure was repeated three to four times.

The residue from the final evacuation was dissolved in 5 ml methylene chloride. Yellow crystals precipitated upon standing. The crystals were filtered, washed with methylene chloride and dried under vacuum. X-ray crystallographic analysis showed that the compound corresponds to:

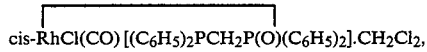

cis-RhCl(CO) [(C_6H_5)_2PCH_2P(O)(C_6H_5)_2].CH_2Cl_2, which contains a Rh to O bond. The infrared spectrum displayed a single intense bond at 1990 $cm^{-1}$ due to the presence of coordinated CO to Rh in the complex.

The above procedure was followed exactly using $(C_6H_5)_2P(CH_2)_nP(O)(C_6H_5)_2$; in which n was 2, 3 and 4 and for $(C_6H_5)_2P(CH_2)_nC(O)OC_2H_5$ in which n was 2. In all instances yellow crystals were recovered which gave infrared spectra similar to the first complex described above, having an intense band at 1990 cm$^{-1}$ indicating the formation of the similar structure. The complex products produced had the formulas:

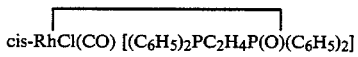

cis-RhCl(CO) [$(C_6H_5)_2PC_2H_4P(O)(C_6H_5)_2$]

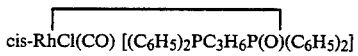

cis-RhCl(CO) [$(C_6H_5)_2PC_3H_6P(O)(C_6H_5)_2$]

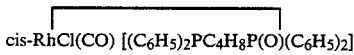

cis-RhCl(CO) [$(C_6H_5)_2PC_4H_8P(O)(C_6H_5)_2$]

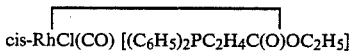

cis-RhCl(CO) [$(C_6H_5)_2PC_2H_4C(O)OC_2H_5$]

The dicarbonyl compounds of the above were prepared by reacting a portion of each of the above monocarbonyl compounds, respectively under CO pressure. Infrared spectra showed the formation of the dicarbonyl compounds had been achieved by the presence of two intense bands, typically at 2090 cm$^{-1}$ and 2010 cm$^{-1}$.

I claim:

1. A process for the production of carboxylic acid anhydrides of the formula RC(O)O(O)CCH$_3$ which comprises the catalytic reaction of a methyl carboxylate ester of the formula RC(O)OCH$_3$ and carbon monoxide in contact with a homogeneous catalyst system consisting essentially of rhodium metal atom, a phosphorus containing ligand in which there is present at least one oxo oxygen atom attached to a phosphorus atom or a carbon atom to form a Z group and the

group in said Z group is located at least one carbon atom removed from the phosphorus atom of the molecules represented by the formulas

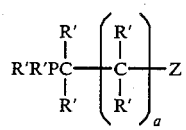 (V)

or

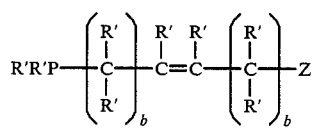 (VI)

and a halogen source; wherein R is an alkyl group having from 1 to 30 carbon atoms, or aryl, aralkyl or alkaryl groups having 6 to 10 ring carbon atoms with from 1 to 10 carbon atoms in the alk-moiety thereof, or alkenyl having from 2 to 30 carbon atoms; R' is aryl, aralkyl or alkaryl having from 6 to 10 ring carbon atoms and the alkyl moiety of said aralkyl or alkaryl group having from 1 to 10 carbon atoms, or an alkyl group having from 1 to 10 carbon atoms; and wherein 1 or more of said R' groups can be substituted with a Z group but not more than 3 of said R' groups in the molecule are so substituted; a is an integer from 0–4; b is an integer from 0–3; and Z is a member selected from the group consisting of

wherein R" is R' or —H and said reaction is carried out under mild reaction conditions.

2. A process as claimed in claim 1 wherein the process is carried out at a reaction temperature up to about 160° C. and a reaction pressure up to about 450 psig.

3. A process as claimed in claim 1 wherein the reaction temperature is from about 50° C. to 150° C.

4. A process as claimed in claim 1 wherein the reaction temperature is from about 105° C. to 125° C.

5. A process as claimed in claim 1 wherein the reaction pressure is from about 50 to 350 psig.

6. A process as claimed in claim 1 wherein Z is

7. A process as claimed in claim 1 wherein Z is —C(O)OR".

8. A process as claimed in claim 1 wherein Z is —C(O)R".

9. A process as claimed in claim 1 wherein the number of C atoms in the linear claim between the P atom and the Z group is from 2 to 4.

10. A process as claimed in claim 1 wherein the halogen source is lithium iodide.

11. A process as claimed in claim 1 wherein the halogen source is a mixture of lithium iodide and methyl iodide.

12. A process as claimed in claim 10 wherein the mole ratio of LiI to Rh is from about 128:1 to 1:1.

13. A process as claimed in claim 11 wherein the mole ratio of LiI to CH$_3$I is from about 10:1 to 1:10.

14. A process as claimed in claim 13 wherein the mole ratio of LiI to Rh is from about 128:1 to 1:1.

15. A process as claimed in claim 1 wherein RC(O)OCH$_3$ is methyl acetate.

16. A process as claimed in claim 1 wherein R' is phenyl.

17. A process as claimed in claim 1 wherein the ligand is Ph$_2$P(CH$_2$)$_2$P(O)Ph$_2$, wherein Ph is phenyl.

18. A process as claimed in claim 1 wherein the rhodium atom is supplied as a rhodium carbonyl compound.

* * * * *

UNITED STATES PATENT AND TRADEMARK OFFICE
CERTIFICATE OF CORRECTION

PATENT NO. : 4,563,309
DATED : January 7, 1986
INVENTOR(S) : RICHARD W. WEGMAN

It is certified that error appears in the above-identified patent and that said Letters Patent is hereby corrected as shown below:

In the Abstract, line 6 from the end after "R' is" insert -- H, --.

In Column 4, line 56 after "R'" delete -- or — H --.

In Column 18, line 5 after "R' is" insert -- H, --.

In Column 18, line 20 delete -- or — H --.

Signed and Sealed this

Second Day of October, 1990

Attest:

HARRY F. MANBECK, JR.

*Attesting Officer*  *Commissioner of Patents and Trademarks*